US009238089B2

(12) United States Patent
Chmielewski et al.

(10) Patent No.: US 9,238,089 B2
(45) Date of Patent: Jan. 19, 2016

(54) ABSORBENT STRUCTURE WITH DISCRETE ACQUISITION CELLS

(71) Applicant: Attends Healthcare Products, Inc., Greenville, NC (US)

(72) Inventors: Harry J. Chmielewski, Raleigh, NC (US); Paul M. Ducker, Brunswick, GA (US)

(73) Assignee: Attends Healthcare Products, Inc., Greenville, NC (US)

( * ) Notice: Subject to any disclaimer, the term of this patent is extended or adjusted under 35 U.S.C. 154(b) by 0 days.

(21) Appl. No.: 14/212,754

(22) Filed: Mar. 14, 2014

(65) Prior Publication Data

US 2014/0276509 A1    Sep. 18, 2014

Related U.S. Application Data

(60) Provisional application No. 61/789,444, filed on Mar. 15, 2013.

(51) Int. Cl.
| | | |
|---|---|---|
| *A61F 13/15* | (2006.01) | |
| *A61L 15/58* | (2006.01) | |
| *A61F 13/539* | (2006.01) | |
| *A61L 15/28* | (2006.01) | |
| *A61L 15/40* | (2006.01) | |
| *A61F 13/531* | (2006.01) | |
| *A61F 13/532* | (2006.01) | |
| *A61F 13/53* | (2006.01) | |

(52) U.S. Cl.
CPC .............. *A61L 15/58* (2013.01); *A61F 13/531* (2013.01); *A61F 13/539* (2013.01); *A61L 15/28* (2013.01); *A61L 15/40* (2013.01); *A61F 13/5323* (2013.01); *A61F 2013/530116* (2013.01); *A61F 2013/530489* (2013.01); *A61F 2013/530496* (2013.01)

(58) Field of Classification Search
CPC ........ A61F 2013/530182; A61F 2013/530496; A61F 2013/530656; A61F 2013/530804; A61F 13/5323; A61F 2013/530116; A61F 2013/530124; A61F 2013/530489
USPC ................................................... 604/358, 367
See application file for complete search history.

(56) References Cited

U.S. PATENT DOCUMENTS 5,593,399 A      1/1997  Tanzer et al.
6,037,518 A  *  3/2000  Guidotti et al. ............... 604/378
(Continued)

FOREIGN PATENT DOCUMENTS

WO          WO 9605790 A1  *  2/1996  .............. A61F 13/15

OTHER PUBLICATIONS

International Search Report and Written Opinion for corresponding PCT application No. PCT/US2014/028292.

*Primary Examiner* — Lynne Anderson
*Assistant Examiner* — Bradley Philips
(74) *Attorney, Agent, or Firm* — Wood, Phillips, Katz, Clark & Mortimer (57) ABSTRACT

An absorbent structure including a composite absorbent laminate is disclosed, with the structure suitable for use in disposable absorbent products such as for infant or incontinence care. Notably the laminate comprises discrete acquisition cells each comprising particles of preferably cellulosic absorbent material. The absorbent structure further comprises particulate superabsorbent polymer which can either be blended with the particulate discrete acquisition cells in the absorbent laminate, or provided in a separate absorbent layer of the absorbent structure. The discrete acquisition cells desirably generate free volume for rapid capillary absorption in an ultra-thin absorbent structure.

11 Claims, 1 Drawing Sheet

(56) References Cited

U.S. PATENT DOCUMENTS

| | | |
|---|---|---|
| 6,191,340 B1 * | 2/2001 | Carlucci et al. ............... 604/369 |
| 6,372,953 B1 * | 4/2002 | Young et al. .................. 604/369 |
| 6,380,456 B1 | 4/2002 | Goldman |
| 6,455,114 B1 * | 9/2002 | Goldhirsch et al. ......... 428/34.7 |
| 6,610,903 B1 * | 8/2003 | Latimer et al. ................ 604/378 |
| 6,746,976 B1 | 6/2004 | Urankar et al. |
| 8,039,684 B2 * | 10/2011 | Guidotti et al. ............... 604/378 |

* cited by examiner

ABSORBENT STRUCTURE WITH DISCRETE ACQUISITION CELLS

FIELD OF THE INVENTION

The present invention relates generally to disposable absorbent products such as infant diapers, adult incontinence briefs, pull-up underwear and bladder control pads, and more particularly to an absorbent structure including discrete, particulate acquisition cells, positioned in operative association with associated absorbent components of the structure, with the cells functioning to provide liquid-acquisition characteristics upon introduction of liquid into the structure to avoid leakage prior to the absorption of the liquid by the associated components.

BACKGROUND OF THE INVENTION

Disposable absorbent products have met with widespread acceptance in the marketplace for a variety of applications, including infant and adult incontinence care, in view of the manner in which such products can provide effective and convenient liquid absorption and retention while maintaining the comfort of the wearer. However, experience has shown that a need exists for thinner, more discreet, garment-like products that can be highly resistant to leakage in use. Absolute confidence in leakage performance of adult products is important because of a risk of embarrassment in public.

There has been a move toward thinner cores of higher density generating structures that have less free volume than conventional wood pulp fluff/superabsorbent polymer (SAP) cores. The free volume required for rapid capillary absorption in an ultra-thin core can be less than the volume of liquid that it is required to contain. Superabsorbent polymers in an ultra-thin core can ultimately absorb large quantities of liquid, but diffusion of liquid into a superabsorbent polymer is slow and typically requires several minutes. This invention provides a means to generate free volume in an ultra-thin absorbent core, on demand, for rapid absorption of liquid in response to wetting.

SUMMARY OF THE INVENTION

In accordance with the present invention, the provision of an absorbent structure including discrete acquisition cells (DACs) solves the above-described problems by providing free volume for rapid capillary absorption in an ultra-thin structure, on demand, as the structure absorbs liquid. This is done by incorporating discrete particles of a cellulosic material that can rapidly increase in at least one dimension when they come in contact with liquid. In most cases, particles made from higher basis weight materials and applied at an effective basis weight less than the basis weight of the material from which the particles were made perform much better than a coherent sheet of the same material at the same effective basis weight. This is because more free volume can be generated by larger particles randomly oriented in the structure. Additionally the capillary structure of this additional free volume can be adjusted by adjusting the particle size distribution of the DAC particles resulting in greater or lesser capillary suction from the voids between the particles. It is additionally desirable that DAC's have a rapid rate of freeswell absorbency. A material that is divided into granules or particles has a greater surface area/volume ratio in principle allowing fluid greater access to the material.

In addition to this, granular or particulate materials can be fed by any of volumetric or gravimeric means well known to those skilled in the art into a moving web to form an absorbent material with any desired basis weight of DAC material by simply adjusting the feed. Conversely monolithic sheet of the desired material that is not divided into particles, but rather fed as a sheet would not be freely adjustable to the desired basis weight. When used in conjunction with absorbent cores made using superabsorbent polymer particles, application of DAC's can piggyback on the well-developed technological infrastructure devoted to adding SAP.

In accordance with the present invention, an absorbent structure is disclosed comprising a composite absorbent laminate comprising a carrier substrate, and a matrix of adhesive filament and discrete acquisition cells each comprising particulate, preferably cellulosic, absorbent material. The discrete acquisition cells are maintained in a randomized configuration on the substrate by the adhesive filaments. The cellulosic discrete acquisition cells can comprise at least one of: compressed cellulosic sponge particles; compressed, cross-linked or uncross-linked wood pulp fibers; creped tissue and paper; and shredded paper. Non-cellulosic discrete acquisition cells may comprise particles of compressed, synthetic fibers. Compressed particles can be dimensionally stabilized in dry form with the addition of a binding agent such as microcrystalline cellulose. The carrier substrate preferably comprises first and second tissue layers between which the matrix of adhesive filaments and discrete absorbent cells is positioned.

In the preferred form, the absorbent structure comprises superabsorbent polymer particles. Notably, the discrete acquisition cells exhibit capillary suction that is less than a capillary suction exhibited by the particles of superabsorbent polymer.

In one form of the invention, the superabsorbent polymer particles are blended in the matrix of said adhesive filaments and discrete acquisition cells. In an alternate form, the absorbent structure comprises an absorbent layer having the superabsorbent polymer particles, with absorbent layer being positioned in liquid-transferring relationship with said composite absorbent laminate having the discrete acquisition cells.

In one specific embodiment, the particulate absorbent material of said discrete acquisition cells comprises compressed, particulate sponge material. In sheet form, the sponge material exhibits a basis weight of about 400 grams per square meter, with the particulate sponge material in said absorbent matrix having an effective basis weight in the range of about 25-100 grams per square meter.

Depending upon the selected composition of the discrete acquisition cells, the particulate absorbent material of said discrete acquisition cells exhibits greater dimensional expansion, upon wetting, in one dimension than in another dimension.

In another aspect of the present invention, an absorbent structure is provided which comprises a composite absorbent laminate comprising: (1) a carrier substrate comprising first and second tissue layers, (2) a matrix of adhesive filaments, and (3) discrete acquisition cells each comprising particulate absorbent material. The discrete acquisition cells are maintained in a randomized configuration between the first and second tissue layers of the substrate by the adhesive filaments. The absorbent structure preferably further comprises superabsorbent polymer particles, wherein the discrete acquisition cells exhibit capillary suction that is less than a capillary suction exhibited by the particles of superabsorbent polymer.

In accordance with the present invention, the superabsorbent polymer particles can either be blended in the matrix of said adhesive filaments and the discrete absorbent cells, or alternately, the absorbent structure can include an absorbent layer having the superabsorbent polymer particles, with the absorbent layer being positioned in liquid-transferring relationship with said composite absorbent laminate.

Other features and advantages of the present invention with become readily apparent from the following detailed description, the accompanying drawings, and the appended claims.

DETAILED DESCRIPTION OF THE INVENTION

While the present invention is susceptible of embodiment if various forms, there is shown in the drawings and will hereinafter be described presently preferred embodiments of the invention, with the understanding that the present disclosure is intended as an exemplification of the invention, and is not intended to limit the invention to the specifics embodiments disclosed herein.

In accordance with the present invention, the provision of an absorbent structure including discrete acquisition cells solves the problems by providing free volume for rapid capillary absorption in an ultra-thin absorbent structure, on demand, as the structure absorbs liquid. This is done by incorporating discrete particles of a material that can rapidly increase in at least one dimension when they come in contact with liquid. In most cases, particles made from higher basis weight materials and applied at an effective basis weight less than the basis weight of the material from which the particles were made perform much better than a coherent sheet of the same material at the same effective basis weight. This is because more free volume can be generated by larger particles randomly oriented in the structure. Furthermore, it is not always practical to make a coherent sheet of the desired materials at the lower effective basis weights desired for application in an absorbent core.

In accordance with the present invention, an absorbent structure is disclosed comprising a composite absorbent laminate comprising a carrier substrate, and a matrix of adhesive filament and discrete acquisition cells each preferably comprising particulate cellulosic absorbent material. The discrete acquisition cells are maintained in a randomized configuration on the substrate by said adhesive filaments. The discrete acquisition cells comprising cellulosic material may comprise at least one of: compressed cellulosic sponge particles; compressed, cross-linked or uncross-linked wood pulp fibers; creped tissue and paper; and shredded paper. Discrete acquisition cells of non-cellulosic material may comprises particles or fragments of compressed, synthetic fibers. Compressed particles can be dimensionally stabilized in dry form with the addition of a binding agent such as microcrystalline cellulose. In the preferred form, the carrier substrate preferably comprises first and second tissue layers between which the matrix of adhesive filaments and discrete acquisition cells is positioned.

In the preferred practice of the invention, the absorbent structure having the composite absorbent laminate comprises superabsorbent polymer particles. Notably, the discrete acquisition cells exhibit capillary suction that is less than a capillary suction exhibited by particles of superabsorbent polymer. In one form of the invention, the superabsorbent polymer particles are blended in the matrix of adhesive filaments and discrete acquisition cells. In an alternate form, the absorbent structure comprises an absorbent layer having the superabsorbent polymer particles, with absorbent layer being positioned in liquid-transferring relationship with said composite absorbent laminate.

In one specific embodiment, the particulate absorbent material of the discrete acquisition cells comprises compressed, particulate sponge material, wherein in sheet form the sponge material exhibits a basis weight of about 400 grams per square meter. The particulate sponge material in the absorbent matrix has an effective basis weight in the range of about 25-100 grams per square meter.

Depending upon the selected composition of the discrete acquisition cells, the particulate absorbent material of said discrete acquisition cells exhibits greater dimensional expansion, upon wetting, in one dimension than in another dimension. Preferably, a pile of particulate or granule cellulosic material of said discrete acquisition cells exhibits a free swell capacity of at least about 8 grams/gram, and a Centrifuge Retention Capacity of less than about 5 gram/gram. The free swell capacity and absorption under pressure of a pile of said particulate cellulosic material of said discrete acquisition cells, when hydrated, can retain approximately two times as much liquid as an equivalent quantity of parent cellulosic material in undivided form. DAC's exhibit relatively large, instantaneous increases in volume when wetted, unlike fluff pulp which collapses when wetted. Like fluff pulp, however, DAC's reach more than 90% of their free swell capacity and absorption under pressure in less than 60 seconds, and liquid spreads spontaneously through the dry particulate material. A low centrifuge retention capacity distinguishes said discrete cellulosic acquisition cells from superabsorbent polymers. Superabsorbent polymers have centrifuge retention values greater than about 25 g/g. The range of volume of individual DAC particles or granules is of the order of 1 mm$^3$ to 10 mm$^3$ before wetting. Upon wetting they experience a large dimensional change in one dimension to instantaneously generate particles of high aspect ratio which prise adjacent particles and surfaces apart to provide unexpectedly large increases in the free volume between DAC's in a laminate structure.

Additionally, the particulate cellulosic material reaches at least 90% of its free swell capacity in less than 60 seconds. The material is selected to be water wettable, such that liquid spreads spontaneously through the dry particulate material. In another aspect of the present invention, an absorbent structure is provided which comprises a composite absorbent laminate comprising: (1) a carrier substrate comprising first and second tissue layers, (2) a matrix of adhesive filaments, and (3) discrete acquisition cells each comprising particulate absorbent material. The absorbent structure further comprises superabsorbent polymer particles, wherein the discrete acquisition cells exhibit capillary suction that is less than a capillary suction exhibited by said particles of superabsorbent polymer. The superabsorbent polymer particles can either be blended in the matrix of said adhesive filaments and the discrete acquisition cells, or alternately, the absorbent structure can include an absorbent layer having the superabsorbent polymer particles, with the absorbent layer being positioned in liquid-transferring relationship with said composite absorbent laminate.

Figure 1:
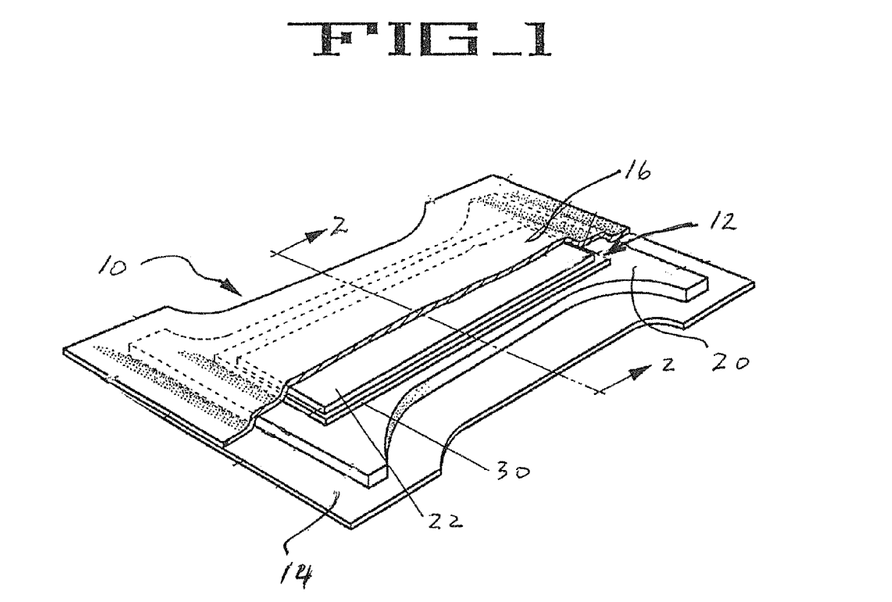
FIG. 1 a diagrammatic, perspective view of a disposable absorbent article configured in accordance with the present invention.
Figure 2:
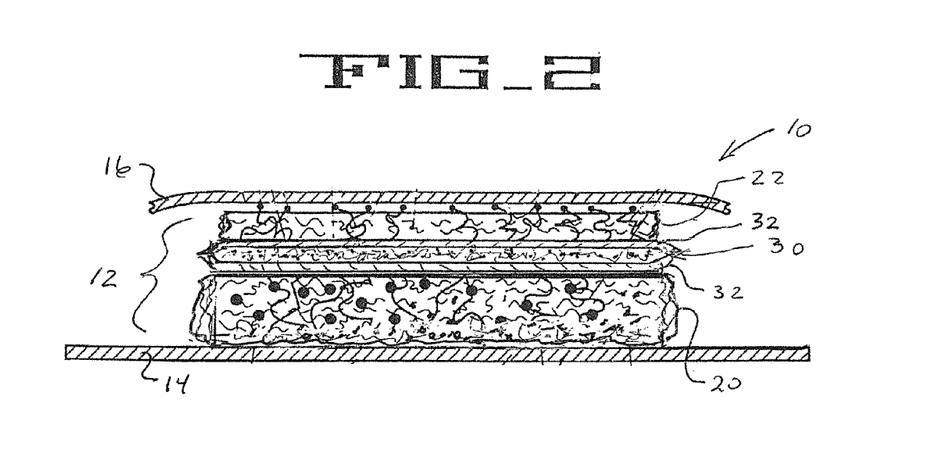
FIG. 2 is a diagrammatic, cross-sectional view of the absorbent article shown in FIG. 1.

With reference now to FIGS. 1 and 2, therein is illustrated in an exemplary absorbent article 10 having an absorbent structure 12 configured in accordance with the present invention. Absorbent article 10 is a diagrammatic illustration of a typical disposable absorbent article or garment for infant or incontinence care. To this end, the absorbent article 10 includes a typically liquid-impervious back sheet 14 positioned beneath the absorbent structure 12, and a liquid-permeable top sheet 16 positioned on top of the absorbent structure.

In the typical construction, as illustrated, the absorbent structure of the article 10 includes a lower, absorbent core 20, typically comprising comminuted wood pulp, i.e., wood pulp fluff, and particulate superabsorbent (SAP) material. In accordance with a typical structure, the absorbent structure 12 further includes an upper acquisition/distribution layer (ADL) 22, positioned beneath top sheet 16. Acquisition layer 22 may comprise a synthetic nonwoven material, including an apertured polymeric film, which acts to receive liquid, and distribute liquid within the absorbent structure or article. Thereafter, liquid is received and absorbed by the absorbent core 20, with the superabsorbent polymer particulate material in the absorbent core acting to absorb and retain the liquid.

In accordance with the present invention, the absorbent structure 12 includes a composite absorbent laminate 30 operatively positioned between the acquisition layer 22 and the absorbent core 20, in liquid-transferring relationship therewith.

Absorbent core 20 could also be any layer of stabilized SAP particles, or absorbent core 20 may not be required at all for some products.

The composite absorbent laminate 30 preferably comprises a substrate in the form of first and second tissue layers 32 with a matrix of filamentary or fibrous adhesive, and discrete acquisition cells (DACs) positioned between the tissue layers 32. The discrete acquisition cells preferably comprise particles or fragments of cellulosic absorbent materials, including but not limited to, compressed cellulosic sponge particles; compressed, cross-linked wood pulp fibers; creped tissue and paper; and shredded paper. Discrete acquisition cells of non-cellulosic material may comprise, for example, particles or fragments of compressed, synthetic fibers. The filamentary adhesive of the composite laminate desirably acts to stabilize the discrete acquisition cells in the laminate, while simultaneously adhering and integrating the tissue layers 32.

Formation of the composite absorbent laminate, including particulate discrete acquisition cells, can be effected in accordance with the teachings of U.S. Patent Publication No. 2011/0162989, to Ducker et al., the disclosure of which is hereby incorporated by reference. This publication discloses formation of an absorbent laminate comprising tissue layers, filamentary adhesive, and particulate superabsorbent polymer.

As discussed, the composite absorbent laminate 30, including the discrete acquisition cells, desirably functions to provide free volume for rapid capillary absorption in an ultra-thin absorbent structure, on demand, as the structure absorbs liquid through top sheet 16, acquisition layer 22, and into the lower absorbent core 20. This specific configuration of the absorbent laminate 30 in order to provide functioning in this manner, is discussed further hereinafter.

In one example of the present invention, discrete acquisition cells are formed from a compressed sponge material that has a basis weight of about 400 grams per square meter (gsm). As used for the discrete acquisition cells, the particles in the structure are provided at an effective basis weight of only 25-100 grams per square meter. It is not technically feasible to process coherent films or webs of this type of material at such low basis weights. In this example, sponge particles were formed to have a mean particle size of about 5 mm×1 mm×1 mm i.e. length×width×thickness).

The discrete acquisition cells are particles that absorb liquid rapidly and provide a large, abrupt increase in at least one dimension when they come in contact with liquid. Except for particles of superabsorbent polymers, which absorb very large quantities of liquid, most hydrophilic materials will absorb only a fraction of their weight in liquid and swell less than 35% in any one direction. An isotropic sheet of regenerated cellulose, for example, will experience about a 35% total volume increase with increases in X, Y, and Z dimensions, whereas an oriented cotton fiber will swell 10-15% in a radial direction but only a 1-2% in the longitudinal direction.

Nonetheless, some special materials exhibit larger dimensional changes in one dimension than would be expected as a result of the absorption of liquid. Furthermore, when these special materials are randomly oriented in particulate form they can create a structure that creates instantaneous free volume in the spaces between hydrated particles. Liquid fills the spaces between particles rapidly due to capillary forces. This type of absorption occurs much more rapidly than the relatively slow diffusion of liquid into a superabsorbent polymer. Capillary absorption in a discrete acquisition cell structure occurs on a time scale of 1-5 seconds whereas diffusion absorption in a superabsorbent polymer occurs on a time scale of 5-10 minutes. While there are some superabsorbent polymer materials that absorb liquid very fast, they have other negative characteristics and are not in widespread use in absorbent products. Among these negatives is that these superabsorbent polymers gel block during hydration and are not effective for handling high-volume, multiple doses of liquid. Again, discrete acquisition cells in accordance with the present invention preferably exhibit nearly instantaneous increase in one dimension of a particle when contacted with liquid and can absorb high-volume, multiple doses of liquid.

Particles of absorbent material made from higher basis weight sheets provide functionality in a laminate that is not possible with uniform layers of the material at the same effective basis weight. This is because a random orientation of discrete particles provides for a 3-dimensional area change, or a volume increase, which is not possible with a thin oriented sheet of the same material.

An important advantage of discrete acquisition cell structures over fast-absorbing SAP's is that over time, liquid partitions from the free volume in the discrete acquisition cell structure to the associated superabsorbent polymer in the absorbent structure, regenerating free volume in the laminate for effective acquisition of multiple doses of liquid. Fast-absorbing SAP's do not function in this manner, and do not work well for multiple doses of liquid.

As noted, absorbent structures formed in accordance with the present invention include discrete acquisition cells that are mixed or blended with particulate superabsorbent, or discrete acquisition cells provided in a separate laminate, either of which can be efficiently formed by a process which adhesively laminates particles between layers of tissue or nonwoven fabric. It is contemplated the formation process itself can include means for compressing and binding discrete acquisition cells DAC's in situ.

Thus, the composite absorbent laminate of the present invention includes three component: upper and lower layers (of tissue or nonwoven), and an adhesively-bound absorbent layer comprised of superabsorbent polymer particles and discrete acquisition cells, or discrete acquisition cells alone.

Materials for laminate are porous tissue, adhesive, and superabsorbent polymer. Materials for discrete acquisition cells include compressed cellulosic sponge (processed by Industrial Commercial Supply, Akron, Ohio), creped tissue, creped paper (Domtar), cellulosic acquisition fiber and other cellulosic materials. It is within the purview of the present invention that the discrete acquisition cells be formed of non-cellulosic materials, including synthetic fibers such as crimped polyester fibers cut from a continuous fiber tow.

Absorbent particles can be compressed and held together with superabsorbent particles, micro-crystalline cellulose (as in medicinal tablets), high molecular weight glycols, and other binders which provide rapid dissolution on wetting. Compressed, resilient polyester fibers could be bound together under compression with micro-crystalline cellulose powder and cut into discrete acquisition cells for processing into a SAP/DAC laminate.

An increase in the dimension of randomly oriented particulates in a thin absorbent structure creates free volume for rapid liquid uptake. Run-off Test and Demand Absorbency Test (GATS) provide key measures of performance.

To produce the composite absorbent laminate 30 of the present invention, hot melt adhesive is used to laminate a substantially continuous layer of particles between two layers of tissue substrates to form a sandwich structure.

In a preferred practice, the laminate of the present invention is made by forming the adhesive into microfibers or filaments using one of the meltblown processes commercially available from hot melt equipment manufacturers such as Nordson or ITW Dynatec to produce a random curtain of hot melt adhesive microfibers, and then mixing those fibers with discrete acquisition cell particles, and optionally with superabsorbent polymer particles which have been metered by any one of the volumetric or gravimetric metering equipment commercially available by equipment suppliers such as K-Tron or Acrison. Forming the particles into a flattened falling stream and mixing it with the flat curtain of adhesive fibers produced by the hot melt equipment produces a uniform basis weight. This mixture is deposited onto a moving tissue substrate and then another tissue substrate is placed on top of the tacky mixture which the adhesive fibers are still tacky to form a sandwich.

The preferred hot melt adhesive is desirably a pressure-sensitive hot melt adhesive of a type designed and suitable for use in construction of absorbent hygiene articles made in typical high-speed converting processes.

In a preferred embodiment, the hot melt application equipment provides a sufficient degree of fiber attenuation and available glue fiber surface in order to capture the particles so that few are unattached. It has been found that typical commercial application equipment is easily capable of this when set up by those skilled in the art.

The superabsorbent polymer can be any type designed for use in disposable absorbent articles well known to those skilled in the art used as supplied by the manufacturers. These commercially available superabsorbent polymer types are generally designed to work well in wood pulp fluff/SAP cores and have particle size distributions that are designed to provide good core permeability (favoring larger particles), but also not easily felt or seen in a diaper product (favoring smaller particles). These commercially available particle size distributions are suitable for use in the dryness layer of the present invention for the same reason they are suitable for use in fluff/SAP cores.

Adhesive content is ideally kept to a minimal level. Adhesive add-on should not exceed 3.5% of the basis weight of the SAP, and more ideally would be kept below 3% of the SAP and even more ideally would be kept below 2% of the SAP basis weight.

Examples and Test Methods
General Laminate Preparation

General Laminate Preparation was made as a continuous web by unwinding a 10.5#3995 tissue substrate with a basis weight of around 17 gsm from Clearwater Paper and feeding it at about 100 meters per minute. SP 507 hot melt adhesive from Savare was melted and processed through an ITW Dynatec hot melt glue system with a UFD head fitted with Omega 5,5 nozzles and sprayed at a roughly 45-degree angle onto the moving tissue web from a distance of about 3-inches. A continuous stream of SAP was continuously metered using volumetric means and was formed into a flattened stream about 10 mm thick directed at a 45-degree angle to intersect with the hot melt adhesive stream at about 20 mm above the web, causing the SAP to mix with the adhesive fibers and be deposited together onto the moving tissue. The SAP was fed at an add-on of 30 gsm.

A second similar layer of SAP and adhesive, again at 30 gsm was deposited in a similar manner on top of the first.

A second layer of 3995 tissue was fed at a rate matching the speed of the continuous web and was laminated Example Laminates Example Laminates listed in each table below as containing either S125D or W112 SAP were made according to General Laminate Recipe 1. In samples listed in each table that contain these SAPs along with DAC's, these were made by taking hand sheet samples of each of these laminates, opening them manually, adding weighed quantities of DAC manually, and re-sealing them manually.

Samples listed in the tables below made with 10SH-PB SAP or made with DAC's and no SAP were made manually as hand sheets using 3995 tissue, SAP, and DAC's as shown. Minimal quantities of 3M spray contact adhesive was used to stabilize these last samples.

Liquid Run-Off

A Liquid Run-Off test was used to obtain a measure of the ability of an absorbent core to rapidly absorb liquid spreading freely over its surface at a 20° incline. Samples of test material were cut to 100 mm by 250 mm and secured to a 150 mm by 300 mm cast acrylic plate, which was then placed on the incline such that the long dimension of the sample was oriented in the direction of the incline. A peristaltic pump was used to dose the samples with 80 ml of a 0.9% saline solution at 7 ml/second. The temperature of the saline solution was 22 degrees C. A dosing tube with an internal diameter of 6.5 mm was positioned 10 mm above and perpendicular to the surface of the sample at the upper end of the incline. A container was placed below the sample to catch the liquid run-off when dosing the sample. Liquid Run-Off was determined by weighing the mass of liquid (+/−0.1 g.) collected in the container. In some tests, Run-Off was determined for a single 80 ml dose. In other tests, the samples were dosed three times, 80 ml per dose, with 30 minutes between each dose; the mass of the liquid runoff was recorded after each dose.

Demand Absorbency (Specific Capacity and Specific Rate of Absorption)

Demand absorbency measured the rate of absorption and capacity of liquid absorbed by Discrete Acquisition Cells (DAC's) as well as parent sheets of materials used to create the DAC's. The test was performed using a Model MK500 Gravimetric Absorbency Test System or GATS manufactured by M/K Systems, Peabody, Mass. A circular sample of 60 mm diameter was cut from a parent sheet of the material and placed in a cylindrical cell. The cylindrical cell had a screen on the bottom to contain the sample. The same cell was used to hold DAC's, which could be added in appropriate amounts to achieve a desired effective basis weight of the material. Constraining weights were placed on the surface of the samples to apply either a 0.3 psi or a nominal pressure to the samples during a test. Demand absorbency of a sample was determined by placing the cylindrical cell containing a sample on a fritted glass plate at 0 mm hydrostatic tension. The 75 mm thick VitraPOR fritted glass plate had a porosity of Class 0 (ISO/4793 P250, 160-250 μm). Specific Capacity (g/g) was determined from the total amount of a 0.9% saline solution at 22 degrees C. absorbed by the test sample divided by the mass of the sample in the cylindrical cell. Specific Rate of Absorption (g/g/sec) was determined from the slope of the linear portion of a chart of mass of liquid absorbed vs. square root of time for demand absorbency.

Free Swell Capacity and Centrifuge Retention Capacity (CRC)

Two grams of dry sample material were placed in an 8 gsm synthetic fiber nonwoven tea bag which was ultrasonically sealed to contain the sample. The sample was soaked in 0.9% saline solution at room temperature for 5 minutes. The bags were hung from a draining rack for 5 minutes and weighed to determine the amount of liquid absorbed. Free Swell Capacity was expressed as mass of liquid absorbed per mass of sample material (+/−0.1 g/g). After that, the bags containing the samples were run through a spin cycle of a Fisher and Paykel Ecosmart Model WA37T26G washing machine for 435 seconds. The spin cycle of the washing machine operated at 670 rpm. The rotor diameter of the washing machine was 10.8 inches. Individual bags containing the samples were reweighed after the spin cycle to determine amount of liquid retained. Centrifuge Retention Capacity was expressed as mass of liquid absorbed per mass of sample material (+/−0.1 g/g).

Dimensional Change during Liquid Absorption

The invention requires materials that preferably exhibit instantaneous and large changes in at least one dimension during absorption of liquid. The compressed sponge DAC used in these examples was a cellulosic sponge from 3M Company, St. Paul, Minn., that had an uncompressed density in the range of 0.040-0.055 g/cc. The material was cut into thin sheets of basis weight in the range of 350-450 gsm and compressed in a proprietary process at Industrial Commercial Supply, Akron, Ohio. The 58 lb. FB paper had a dry tensile strength of 29 and 21 lbs./in., for MD and CD respectively (Tappi T494 Test Method); the porosity was 9 sec/100 cc (Tappi T460 Test Method). The compressed cellulosic acquisition fiber was obtained from a Pampers Cruisers baby diaper manufactured by Procter & Gamble, Cincinnati, Ohio. Other cellulosic acquisition fibers could also be used, providing they exhibited centrifuge retention capacity or water retention values that were less than 65% of the values for conventional fluff pulp fibers. These materials are then reduced to particulate form and used as an absorbent layer in a laminate structure. Materials of a given thickness were cut to 5 mm length×1 mm width in a Clary 2200D, Class 6, paper shredder. Note that the compressed sponge expanded 7.5× its original thickness on wetting and that the high-basis weight creped papers (i.e. 58 lb and 58 lb FB) expanded 1.5-2.1× their original length on wetting.

TABLE 1

Increase in Dimension of DAC's on Wetting

| DAC Material | Relative Length Increase on Wetting | Relative Width Increase on Wetting | Relative Thickness Increase on Wetting |
|---|---|---|---|
| Sponge | Nominal | Nominal | Nominal |
| Compressed Sponge | Nominal | Nominal | 7.5 X |
| 58 lb | Nominal | Nominal | Nominal |
| Creped 58 lb | 2.1 X | Nominal | Nominal |
| 58 lb FB | Nominal | Nominal | Nominal |
| Creped 58 lb FB | 1.5 X | Nominal | Nominal |
| Tissue | Nominal | Nominal | Nominal |
| Creped Tissue | 1.3 X | Nominal | Nominal |
| Compressed Cellulosic Acquisition Fiber | Nominal | Nominal | 4.6 X |

DAC's in Single-layer Laminates and as a Separate Layer

Examples of the use of discrete acquisition cells are given in two configurations: (1) DAC's and SAP were mixed in an absorbent layer and adhesively bonded between two layers of porous tissue; and, (2) a separate adhesively-bonded laminate was made only with DAC's and was placed on top of an adhesively-bonded laminate made only with SAP; both of these laminates were made with porous tissue with a Frazier Porosity of greater than 150 ft3/min/ft2.

6.3.1 DAC's and Superabsorbent Polymer in a Single-layer Laminate 6.3.1.1 Liquid Run-Off Liquid Run-Off of a laminate made with 60 gsm of S125D, a granular superabsorbent polymer exhibiting an intermediate Centrifuge Retention Capacity (CRC) and intermediate rate of absorption compared to those used in the industry, was 50.6 g. out of a possible 80 g. dose (TABLE 2). A pooled standard deviation for these test results was 1.6 g. W211, a granular SAP with a higher rate of liquid absorption than that of S125D, exhibited more Run-Off than the S125D. It was noted that the mean particle size of W211 was significantly greater than that of S125D, i.e. 450 μm for W211 and 380 μm for S125D. Aqua Keep 10SH-PB was a different type of SAP made from an agglomeration of very fine particles. It had a very high rate of liquid absorption and performed well in a Run-Off test. These materials did not, however, perform well after multiple doses of liquid (TABLE 3).

TABLE 2

Effect of DAC Basis Weight in Single-Layer Laminate on Liquid Run-Off

| Sample No. | Type of DAC | DAC BW (gsm) | Absorbent Layer SAP | Mean Particle Size (μm) | SAP BW (gsm) | Mean Run-Off (g) |
|---|---|---|---|---|---|---|
| 1. | None | 0 | S125D | 380 | 60 | 50.6 |
| 2. | None | 0 | W211 | 450 | 60 | 60.1 |
| 3. | None | 0 | 10SH-PB | — | 60 | <1 |
| 4. | Sponge | 25 | S125D | 380 | 60 | 31.3 |
| 5. | Sponge | 50 | S125D | 380 | 60 | 27.0 |
| 6. | Sponge | 100 | S125D | 380 | 60 | 2.1 |

Incorporation of a compressed sponge discrete acquisition cells into a single-layer laminate significantly decreased (i.e. improved) the Run-Off of liquid (TABLE 2). Furthermore, the improvement was a function of the basis weight of the sponge DAC that was incorporated into the laminate with 60 gsm of S125D SAP. For a DAC basis weight of 100 gsm, the mean Run-Off was only 17.5 g. of the total 80 g. applied to the laminate. Note that good levels of performance were achieved in the range of 25-100 gsm of compressed sponge DAC. The basis weight of sheets of compressed sponge used to make the DAC's was about 400 gsm. It would not be possible to provide sheets of the compressed sponge at such low basis weights.

TABLE 3

Multiple-dose Run-Off data (3 × 80 ml doses) for fast absorbing superabsorbent polymer and DAC's in a two-layer laminate structure

| | Run-Off (g) | | | |
|---|---|---|---|---|
| | 1st Dose | 2nd Dose | 3rd Dose | Total |
| One layer of 60 gsm 10SH-PB fast-absorbing superabsorbent polymer | 3 | 41 | 68 | 112 |
| One layer of 50 gsm compressed sponge DAC's & one layer of 60 gsm S125D superabsorbent polymer | 2 | 20 | 35 | 57 |

TABLE 4 shows the effect of SAP basis weight on Run-Off for single-layer laminates made with 50 gsm of the compressed sponge DAC. The Run-Off of a laminate containing 50 gsm of the sponge DAC's, without any superabsorbent polymer, was only a little better than that obtained for the laminates with superabsorbent polymer only. Run-Off was greatly improved when DAC's and superabsorbent were used together in the absorbent layer of the same laminate. These data indicate an unexpected synergistic interaction between the DAC's and SAP in the laminate. The total basis weight of material in the absorbent layer of laminate #5 in TABLE 4 was only 95 gsm, i.e. 50 gsm of DAC and 45 gsm of SAP, and exhibited a Run-Off of 24.4 g. By comparison, a laminate containing 125 gsm of superabsorbent polymer, and no DAC's, had a higher value of Run-Off at 44.8 g.

TABLE 4

Effect of SAP BW in Single-Layer Laminate on Liquid Run-Off

| Sample No. | Type of DAC | DAC BW (gsm) | Absorbent Layer SAP | SAP BW (gsm) | Mean Run-Off (g) |
|---|---|---|---|---|---|
| 1. | None | 0 | S125D | 45 | 45.8 |
| 2. | None | 0 | S125D | 60 | 50.6 |
| 3. | None | 0 | S125D | 125 | 44.8 |
| 4. | Sponge | 50 | None | 0 | 42.3 |
| 5. | Sponge | 50 | S125D | 45 | 24.4 |
| 6. | Sponge | 50 | S125D | 60 | 27.0 |
| 7. | Sponge | 50 | S125D | 125 | 22.7 |

6.3.1.2 Demand Absorbency

A Gravimetric Absorption Test System or Model MK500 GATS manufactured by M/K Systems Inc. was used to measure the rate and extent of liquid absorption of compressed sponge DAC's used in the present invention. TABLE 5 provides a comparison between the parent sheet material and DAC particulates cut from the parent sheet. The basis weight of the parent sheet material was 360 gsm. It was not possible to obtain sheets of this material at a lower basis weight. Discrete acquisition cells cut from the parent sheet were tested at two basis weights. An effective basis weight of 100 gsm was tested because it has been used in preferred embodiments of the current invention and a basis weight of 360 gsm was tested for comparison with the parent sheet at the same basis weight. The tests were done at nominal pressure and at a pressure of 0.3 psi.

At nominal pressure the rate of liquid absorption of the parent sheet was greater than that for the DAC's (TABLE 5). However, at 0.3 psi, a pressure frequently encountered in actual product use, the rate of absorption of the DAC's was greater than that of the parent sheet. A pooled standard deviation for these Specific Rate of Absorption data was 0.02 g/g/sec. Specific liquid absorption capacities (g/g) of the DAC's exceeded those of the parent sheet at both pressures and basis weights. Even under a pressure of 0.3 psi, the demand absorbency of the DAC's was more than 2× that of the parent sheet material. A pooled standard deviation for these Specific Capacity data was 0.3 g/g. These unexpected increases in specific liquid absorption capacities for the DAC's are a fundamental feature of the present invention.

TABLE 5

Demand absorbency of compressed sponge DAC's compared to parent sheet material

| | | Parent Sheet | | Discrete Acquisition Cells (DAC's) | |
|---|---|---|---|---|---|
| Pressure | | 360 gsm | 100 gsm | 360 gsm | 100 gsm |
| Liquid absorbed at nominal pressure | Specific Rate of Absorption (g/g/sec) | 0.17 | — | 0.13 | 0.21 |
| | Specific Capacity (g/g) | 6.3 | — | 7.2 | 18.2 |
| Liquid absorbed at 0.3 psi | Specific Rate of Absorption (g/g/sec) | 0.16 | — | 0.19 | 0.67 |
| | Specific Capacity (g/g) | 3.9 | — | 6.3 | 9.3 |

Liquid Run-Off

TABLE 6 shows the Run-Off obtained for two layers of adhesively-bonded laminates. The upper layer was made with 50 gsm of various DAC's and the lower layer was made with 60 gsm of S125D superabsorbent polymer. No adhesive was used between the laminates. For comparison, Sample #3 in TABLE 6 provides a structure which is typical of conventional technology. Here a 60 gsm layer of a through-air-bonded, or TAB, acquisition/distribution layer, or ADL, was placed on the surface of a laminate made with 60 gsm of S125D SAP. The Run-Off of Sample #3, comprised of an upper layer of Sample #2 and a lower layer of Sample #1, was 40.7 g. The 60 gsm TAB ADL provided some improvement in liquid Run-Off versus Sample #1 with no upper layer at all.

A single layer containing only 50 gsm of the compressed sponge DAC's exhibited a Run-Off of 42.3 g. When that laminate was placed on top of a bottom layer of Sample #1 the Run-Off was reduced to a value of 17.1 g. This was a better result than that of a single laminate comprised of a mixture of 60 gsm SAP and 50 gsm of the compressed sponge DAC's, which exhibited a Run-Off value of 27.0 g. This improvement in Run-Off was due to the performance of the DAC's. It cannot be accounted for by two additional layers of porous tissue in the two-laminate structure.

TABLE 6

Effect of Type of DAC in Separate Layer on Liquid Run-Off

| Sample No. | Upper Layer | BW of Upper Layer (gsm) | Lower Layer SAP | Lower Layer SAP BW (gsm) | Mean Run-Off (g) |
|---|---|---|---|---|---|
| 1. | None | 0 | S125D | 60 | 50.6 |
| 2. | TAB ADL | 60 | None | 0 | 62.6 |
| 3. | TAB ADL | 60 | S125D | 60 | 40.7 |
| 4. | Compressed Sponge | 50 | None | 0 | 42.3 |
| 5. | Compressed Sponge | 50 | S125D | 60 | 17.1 |

TABLE 6-continued

Effect of Type of DAC in Separate Layer on Liquid Run-Off

| Sample No. | Upper Layer | BW of Upper Layer (gsm) | Lower Layer SAP | Lower Layer SAP BW (gsm) | Mean Run-Off (g) |
|---|---|---|---|---|---|
| 6. | Creped Tissue | 50 | S125D | 60 | 11.1 |
| 7. | 58 lb Creped | 50 | S125D | 60 | 18.2 |
| 8. | 58 lb. FB Creped | 50 | S125D | 60 | 17.9 |
| 9. | UFS Uncreped | 50 | S125D | 60 | 25.5 |

Samples #6, #7, and #8 in TABLE 6 compare the Run-Off performance of two-layer structures made with an upper laminate containing DAC's made from creped tissue and creped papers. These combinations provided excellent results. Liquid Run-Off was only 11.1 g. for DAC's made from parent sheets of 20 gsm creped tissue. These creped tissue DAC's are different from the compressed sponge material in that the parent sheet material is available at low basis weight (e.g. 20 gsm).

It was possible to make DAC's from multiple layers of creped tissue so as to increase the thickness of individual DAC particles of creped tissue. This can provide an opportunity to provide DAC's to reduce Run-Off even more than that exhibited by DAC's made from only a single layer of creped tissue.

It is believed that DAC's made from higher basis weights of creped papers may to exert greater forces than tissue on adjacent particles when constrained in an absorbent layer. The Run-Off performance of two different two-layer structures each made with an upper laminate containing DAC's made from different types of a 58 lb/ream creped paper (i.e. about 873 gsm) generated Run-Off values of 18.2 g. and 17.9 g.

Finally, the Run-Off of a two-layer structure made with an upper laminate containing DAC's made from uncoated free sheet (UFS) copy paper of 78 gsm was unexpectedly good at a value of 25.5 g. This paper had not been creped and did not exhibit a large dimensional change on wetting.

TABLE 7

Centrifuge Retention Capacity of Discrete Acquisition Cell Materials

| | Free Swell Capacity (g/g) | Centrifuge Retention Capacity (g/g) |
|---|---|---|
| Compressed Sponge | 20.6 | 1.9 |
| Creped tissue | 15.6 | 1.3 |
| UFS Uncreped | 10.4 | 1.3 |
| Fast 10SH-PB SAP† | 65 | 40 |
| Typical S125D SAP† | 60 | 34 |

†EDANA Test Method WSP 241

From the foregoing, it will be observed that numerous modifications and variations can be effected without departing from the true spirit and scope of the novel concept of the present invention. It is to be understood that no limitation with respect to the specific embodiments disclosed herein is intended or should be inferred. The disclosure is intended to cover, by the appended claims, all such modifications as fall within the scope of the claims.

What is claimed is:

1. An absorbent structure, comprising:
a composite absorbent laminate comprising a carrier substrate, and a matrix of adhesive filaments, and discrete acquisition cells each comprising particulate cellulosic absorbent material comprising at least one of creped tissue and creped paper, said discrete acquisition cells being maintained in a randomized configuration on said substrate by said adhesive filaments, wherein said particulate absorbent material of said discrete acquisition cells exhibits greater dimensional expansion, upon wetting, in one dimension than in another dimension.

2. An absorbent structure in accordance with claim 1, wherein
said particulate cellulosic material of said discrete acquisition cells exhibits a free swell capacity of at least about 8 grams/gram, and a Centrifuge Retention Capacity of less than about 5 gram/gram, wherein said particulate absorbent material exhibits greater dimensional expansion, upon wetting, in one dimension than in another dimension.

3. An absorbent structure in accordance with claim 1, wherein
said particulate cellulosic material of said discrete acquisition cells reaches at least 90% of its free swell capacity in less than 60 seconds.

4. An absorbent structure in accordance with claim 1, wherein
a quantity of said particulate cellulosic material of said discrete acquisition cells, when hydrated, retains approximately 2 times liquid in free swell capacity than an equivalent dry quantity of parent cellulosic material in undivided form.

5. An absorbent structure in accordance with claim 1, wherein
said absorbent structure comprises superabsorbent polymer particles, said discrete acquisition cells exhibiting capillary suction time that is less than a capillary suction time exhibited by said superabsorbent polymer particles.

6. An absorbent structure in accordance with claim 5, wherein
said superabsorbent polymer particles are blended in said matrix of said adhesive filaments and said discrete absorbent cells.

7. An absorbent structure in accordance with claim 5, wherein
said absorbent structure comprises an absorbent layer having said superabsorbent polymer particles, said absorbent layer being positioned in liquid-transferring relationship with said composite absorbent laminate.

8. An absorbent structure in accordance with claim 1, wherein
said carrier substrate comprises first and second tissue layers between which said matrix of said adhesive filaments and said discrete absorbent cells is positioned.

9. An absorbent structure, comprising:
a composite absorbent laminate comprising : (1) a carrier substrate, said carrier substrate comprising first and second tissue layers, (2) a matrix of adhesive filaments, and (3) discrete acquisition cells each comprising particulate absorbent material comprising at least one of creped tissue and creped paper, said discrete acquisition cells being maintained in a randomized configuration between said first and second tissue layers on said substrate by said adhesive filaments,
said absorbent structure comprising superabsorbent polymer particles, said discrete acquisition cells exhibiting capillary suction time that is less than a capillary suction time exhibited by said superabsorbent polymer particles, wherein said particulate absorbent material of said discrete acquisition cells exhibits greater dimensional expansion, upon wetting, in one dimension than in another dimension.

10. An absorbent structure in accordance with claim 9, wherein
    said superabsorbent polymer particles are blended in said matrix of said adhesive filaments and said discrete absorbent cells.

11. An absorbent structure in accordance with claim 9, wherein
    said absorbent structure comprises an absorbent layer having said superabsorbent polymer particles, said absorbent layer being positioned in liquid-transferring relationship with said composite absorbent laminate.

* * * * *